United States Patent
Mastoris et al.

(10) Patent No.: US 6,856,409 B2
(45) Date of Patent: Feb. 15, 2005

(54) TOOL AND METHOD FOR EVALUATING A PIN CONNECTOR

(75) Inventors: Steven F. Mastoris, El Dorado Hills, CA (US); Akbar Monfared, Placerville, CA (US); Ian Robert Inglis, Rocklin, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 256 days.

(21) Appl. No.: 10/192,270

(22) Filed: Jul. 9, 2002

(65) Prior Publication Data

US 2004/0008340 A1 Jan. 15, 2004

(51) Int. Cl.⁷ .............................................. G01B 11/24
(52) U.S. Cl. ....................... 356/615; 356/237.1; 29/837
(58) Field of Search ............................. 356/237.1, 614, 356/615; 140/123; 29/837, 830, 740; 439/913, 68

(56) References Cited

U.S. PATENT DOCUMENTS

| | | | | |
|---|---|---|---|---|
| 4,611,399 A | * | 9/1986 | Tavares et al. | 29/876 |
| 4,739,550 A | * | 4/1988 | Schaeffer et al. | 29/741 |
| 4,895,189 A | * | 1/1990 | Alemanni | 140/147 |
| 5,323,105 A | * | 6/1994 | Davis et al. | 324/761 |
| 5,363,551 A | * | 11/1994 | Cottet et al. | 29/837 |
| 6,061,903 A | * | 5/2000 | Lees et al. | 29/837 |

FOREIGN PATENT DOCUMENTS

GB      2208759 A   *   4/1989   ......... H01R/13/631

* cited by examiner

Primary Examiner—Richard A. Rosenberger
Assistant Examiner—Vincent P. Barth

(57) ABSTRACT

A tool for evaluating a pin connector of a backplane preferably includes at least one connector having receptacles for receiving pins of a pin connector of a backplane. The receptacles are open at both ends so that ends of the pins are visible in the receptacles when the tool is seated on the pin connector.

29 Claims, 6 Drawing Sheets

TOOL AND METHOD FOR EVALUATING A PIN CONNECTOR

FIELD OF THE INVENTION

The present invention relates to the field of evaluating pin connectors. More specifically, the present invention relates to a tool and method for evaluating a pin connector on a backplane.

BACKGROUND OF THE INVENTION

Computers and their peripheral devices are used for a wide variety of purposes including, data storage, communication, and document creation. Peripheral Component Interconnect (PCI) is a local bus that is commonly used to connect a computer with one or more peripheral devices. A PCI bus provides a high-speed connection with peripherals and can connect multiple peripheral devices to the host computer. The PCI bus typically plugs into a PCI slot on the motherboard of the host computer.

CompactPCI or "cPCI" was introduced in 1995 based on the PCI standard and has since become one of the fastest-growing industrial bus architectures to date. Initially targeted at the telecommunications and industrial control markets, CompactPCI takes the popular PCI interface and packages it into a smaller, more rugged unit. The most noticeable change made to the architecture was the adoption of a form factor in which all dimensions and mechanical components are standardized by the Institute of Electrical and Electronics Engineers (IEEE). Consequently, numerous vendors can supply mechanically interchangeable components.

One important use of the CompactPCI is in a blade server, also called an ultradense server. Blade servers are comprehensive computing systems that include processor, memory, network connections, and associated electronics, all mounted on a single motherboard called a blade. There are many types of blades—server blades, storage blades, network blades and more.

The server blade, along with storage, networking and other blades, are typically installed in a rack-mountable enclosure that houses multiple blades that share common resources such as cabling, power supplies, and cooling fans. The blades are connected into a common circuit board, called a backplane, that provides connections to and between blades for both data and power. With its modular, hot-pluggable architecture, the easily accessible blade server offers increased computing density while ensuring both maximum scalability and ease of management.

Typically, the backplane provides rows of pins, preferably configured according to the cPCI standard, for connection to the various blades that might be installed in the blade server. The blades each have a corresponding connector that includes receptacles or holes in which the pins of the connector on the backplane are received when the blade is installed. Because of the complex and tightly packed circuitry that may exist on a blade, a large number of connections are required between the blade and the backplane. Consequently, there are a relatively large number of delicate pins provided in each connection row on the backplane that might receive a blade.

The pins are packed close together, preferably according to the cPCI standard, to provide the necessary number of connections within an appropriate amount of real estate on the backplane. In part, because the pins are so closely packed together, the pins are relatively thin and, therefore, somewhat delicate. A pin can easily be bent or broken.

Damage to the pins can occur when a blade is improperly installed. Damage to the pins can also occur during the storage or shipping of the backplane.

If a pin is broken or bent and fails to make a connection with an installed blade, the blade will likely not function properly, and it may be very difficult to identify the problem as bent or missing pin among so many pins on the backplane. Consequently, it would be very useful to be able to verify whether any pins have been bent or broken prior to placing the backplane in service or installing a blade.

SUMMARY OF THE INVENTION

In one of many possible embodiments, the present invention provides a tool for evaluating a pin connector of a backplane. The tool preferably includes at least one connector having receptacles for receiving the pins of a pin connector of a backplane. The receptacles are open at both ends so that ends of the pins are visible in the receptacles when the tool is seated on the pin connector.

In another embodiment, the present invention provides a method of making a tool for evaluating a pin connector of a backplane. The method is conducted by forming at least one connector having receptacles for receiving pins of a pin connector of a backplane, the receptacles being open at both ends so that ends of the pins are visible in the receptacles when the tool is seated on the pin connector.

In another embodiment, the present invention provides a method of evaluating a pin connector of a backplane by attempting to seat a tool on the pin connector, the tool having at least one connector having receptacles for receiving pins of a pin connector of a backplane, the receptacles being open at both ends so that ends of the pins are visible in the receptacles when the tool is seated on the pin connector.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain the principles of the present invention. The illustrated embodiments are examples of the present invention and do not limit the scope of the invention.

Throughout the drawings, identical reference numbers designate similar, but not necessarily identical, elements.

DETAILED DESCRIPTION OF THE PREFERRED EMBODIMENTS

Figure 1:
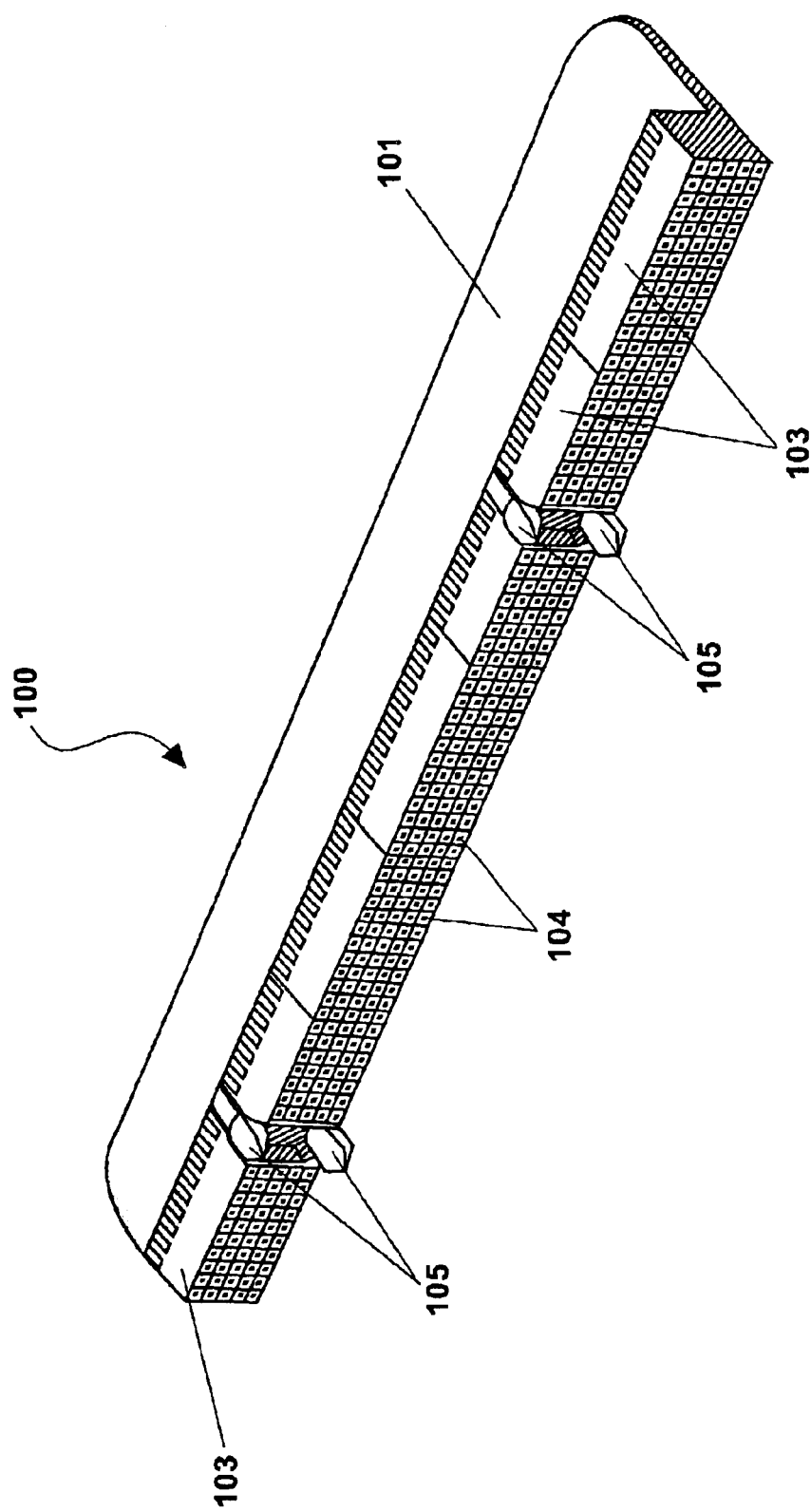
FIG. 1 is an illustration of a tool according to an embodiment of the present invention for evaluating the integrity of pins in a pin connector on a backplane.

FIG. 1 is an illustration of a tool according to an embodiment of the present invention for evaluating the integrity of pins in a pin connector on a backplane. As shown in FIG. 1, the tool (100) preferably includes connector blocks (103) that are arranged in a row corresponding to a row of pins on a backplane for receiving a blade. Alternatively, the connector (103) of the tool (100) may be a single unit from a solid material of similar form factor.

The connectors (103) are secured to a backing plate (101) so that they can be installed or removed as a unit. The backing plate (101) may also function as a handle to facilitate use of the tool (100).

These connectors (103) include holes or receptacles (104) in which the pins of a connector on the backplane are received. Preferably, these receptacles (104) are arranged according to the cPCI standard.

Figure 2:
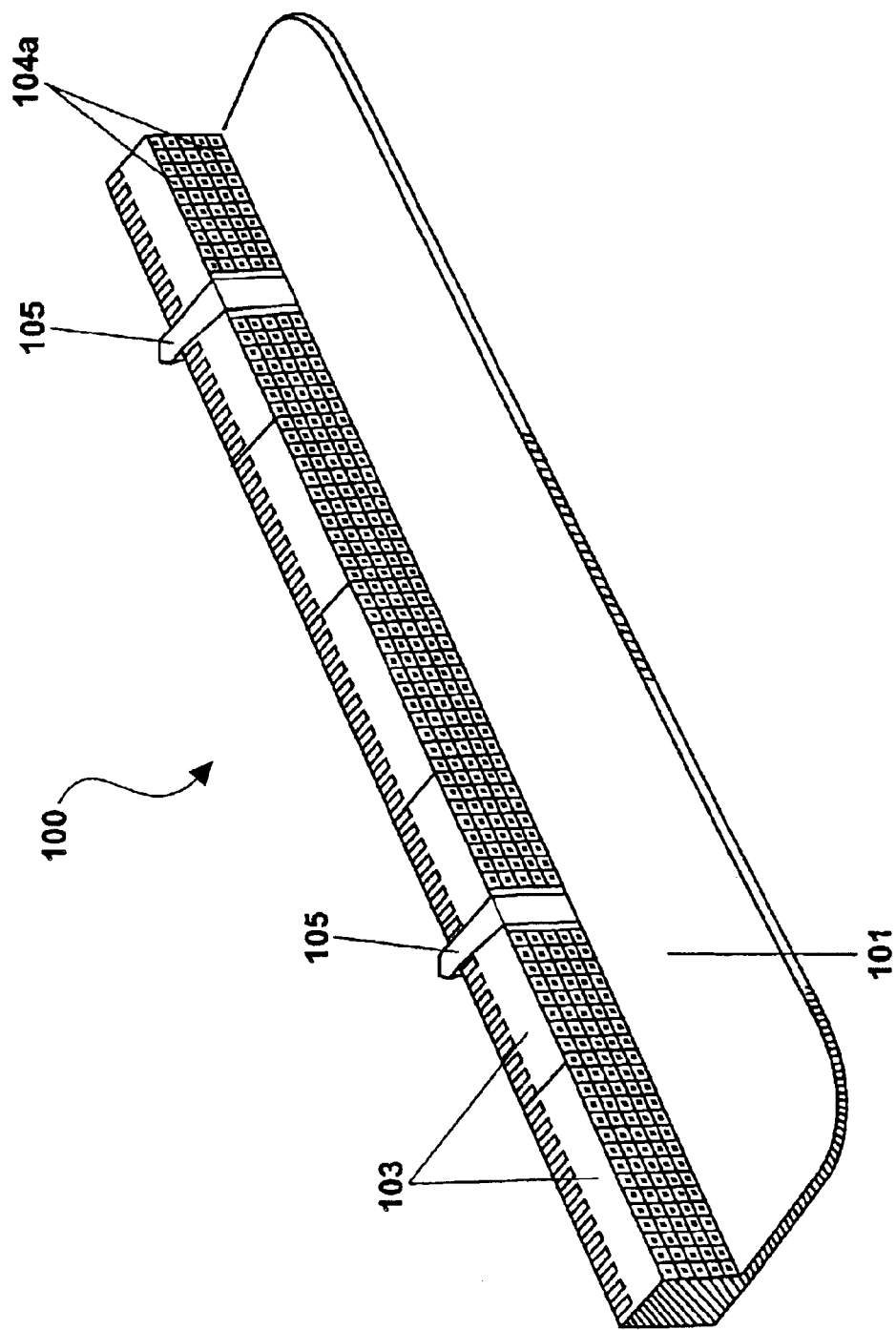
FIG. 2 is another view of the tool of FIG. 1.

FIG. 2 is another view of the tool illustrated in FIG. 1. FIG. 2 provides a view of the opposite side of the connectors (103) from that illustrated in FIG. 1. As shown in FIG. 2, the holes or pin receptacles (104) extend all the way through the connector blocks (103). The opposite ends of the holes (104a) are illustrated in FIG. 2.

The tool (100) is used as follows. When it is necessary to test the integrity of the pins of a pin connector on the backplane, the tool (100) is seated on the pins of the pin connector as if it were a blade being connected to the backplane. It is important to gently seat the tool (100) on the pin connector of the backplane. The tool (100) should not be forced onto the pin connector.

If the tool (100) will not seat properly on the pin connector, that indicates that a pin of the connector is bent and is preventing the tool (100) from seating properly. If the tool (100) does seat properly, the pins of the pin connector will extend through the holes (104). As will be explained below, the ends of the pins can then be examined extending from the openings (104a) of the holes (104). This will reveal if a pin is missing, as opposed to being bent, but still in place.

Returning to FIG. 1, guides (105) may be disposed in between the connectors (103) at various points on the tool (100). On the connector of a blade, these or similar guides would be used to hold a key that is specific to the type of blade on which the keys are installed. These blade keys are matched by corresponding keys in between the connection pins on a connector of the backplane.

This key arrangement insures that only a particular type of blade can be connected to a particular connector on the backplane that is intended for receiving that type of blade. Thus, if a connector on a backplane is designed to receive only a single type of blade, the keys in that backplane connector will prevent any other type of blade from being installed in that connector.

Keys may or may not be loaded into the guides (105) of the tool (100). The use of keys in the tool (100) will be important if corresponding keys are present in the pin connector of the backplane. As the use of the tool (100) includes seating the tool (100) on the pin connector of the backplane, it may be useful to have keys in the tool (100) that match corresponding keys in the backplane connector so that the tool (100) can be properly seated in the same fashion as a blade would be engaged by the pin connector.

The tool (100) can be constructed by taking standard connectors (103), preferably compliant with the cPCI standard, and sizing those connectors (103) down for attachment to the plate (106). This would possibly include cutting the connectors (103) to make sure that the holes (104) extend completely through the connector blocks (103) with such a length that the pins of the pin connector can extend through the holes (104) enough to allow for the detection of a missing pin, as will explained in more detail below. Alternatively, the tool (100) can be constructed from any integration of the various components described above.

Figure 3:
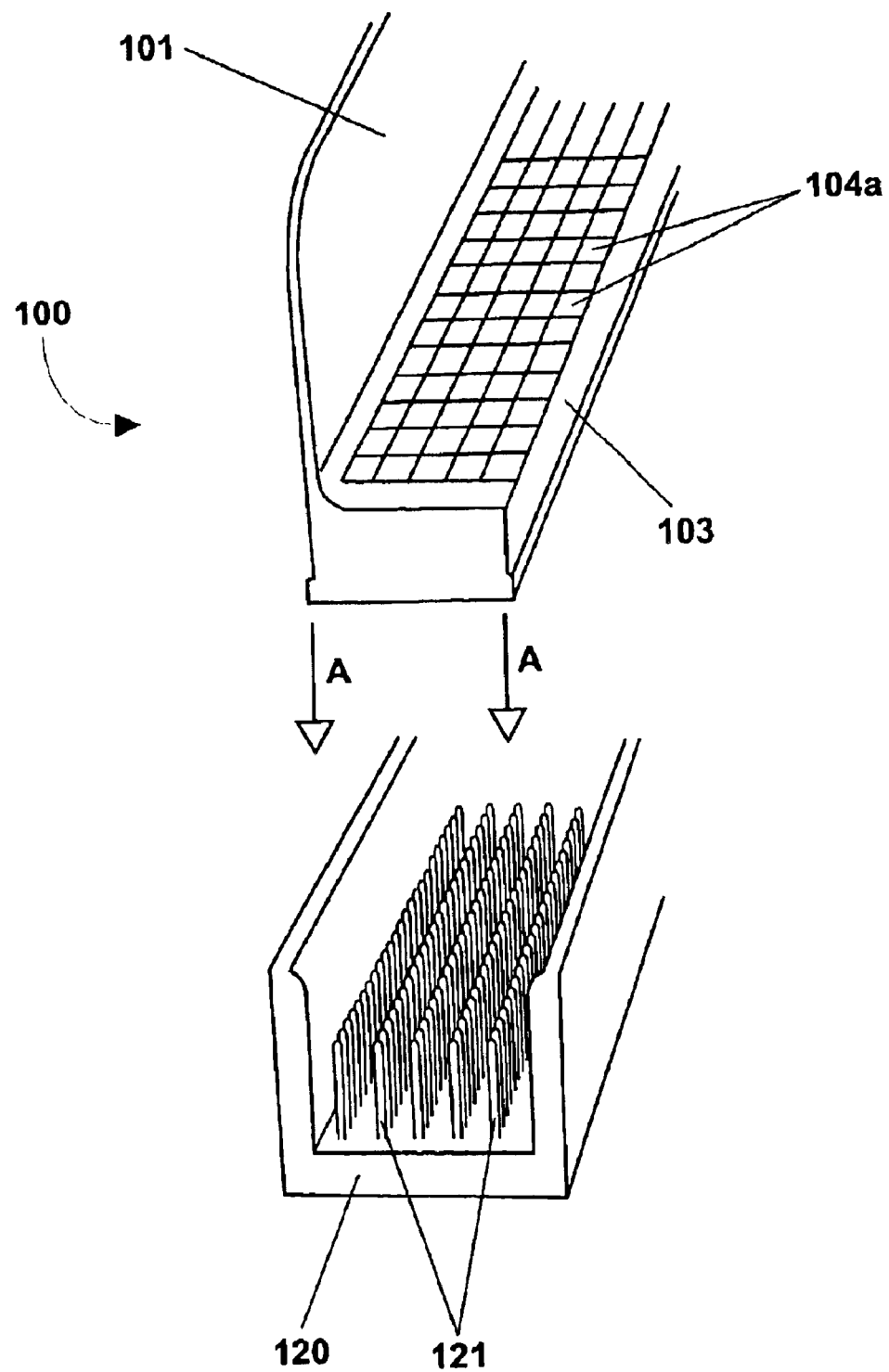
FIG. 3 is an illustration of the tool of FIG. 1 being used on a pin connector of a backplane according to an embodiment of the present invention.

FIG. 3 is an illustration of the tool of FIG. 1 being seated on a pin connector of a backplane according to an embodiment of the present invention. As explained above, the tool (100) of the present invention is used by seating the tool (100) on a pin connector (120) of a backplane. The pin connector (120) is preferably a cPCI connector that is used to attach a blade to the backplane.

Preferably using the back plate (101) as a handle, the user will seat the tool (100) on the connector (120) as shown by the arrows "A". As mentioned above, it is important to not force the tool (100) to seat on the connector (120). As the tool (100) is seated, the pins (121) of the pin connector (102) will be received in the holes of the connectors (103) on the tool (100) and will extend from the upper ends (104a) of those holes when the tool (100) is properly seated on the connector (120).

As mentioned above, if the tool (100) will not seat properly on the connector (120), that indicates that something is preventing the tool (100) from seating. The most likely obstruction preventing the tool (100) from seating would be a bent pin (121) of the connector (120) that has not been received in a hole of the connectors (103) and therefore prevents proper seating of the tool (100). Consequently, if the tool (100) will not seat properly, the connector (120) is likely damaged. The tool (100) is then removed, and the user can examine the connector (120) for a bent pin or other deformity.

In this way, a defective connector (121) can be readily identified before it is placed in service or before a blade is connected thereto. This avoids the difficulty of diagnosing the problems that can be caused by a bent pin after a blade is installed on the connector (120).

Figure 4:
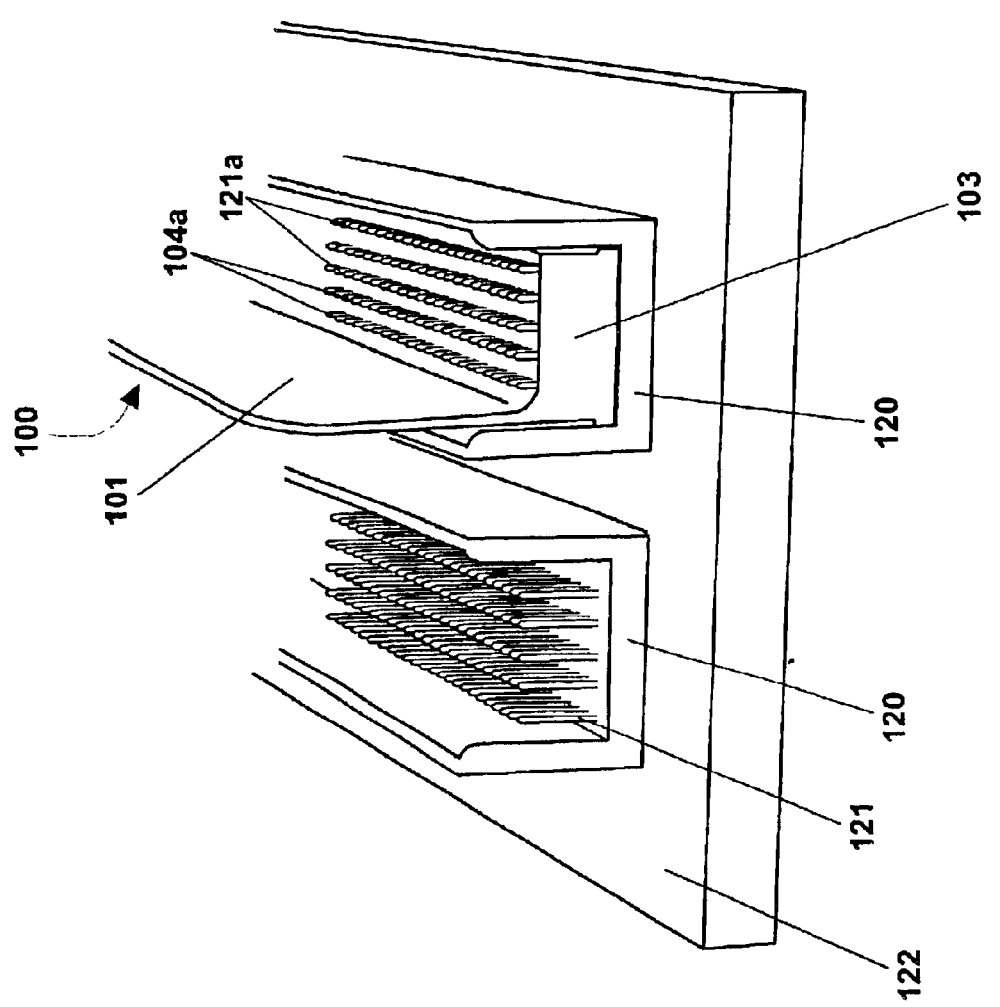
FIG. 4 is an illustration of the tool of FIG. 1 installed on a pin connector of a backplane according to an embodiment of the present invention.

If the tool (100) seats properly, as illustrated in FIG. 4, it can be assumed that no bent pins are present in the connector (120) that would obstruct seating of the tool (100). As shown in FIG. 4, when the tool (100) is properly seated on the connector (120), the ends (121a) of the pins (121) of the connector (120) are visible through the open upper ends of the holes or pin receptacles in the connectors (103) on the tool (100).

As noted above, proper seating of the tool (100) without the need to apply excessive force indicates that the connector (120) very likely does not contain any bent pins that could obstruct seating of the tool (100). However, even if the tool (100) readily seats, the connector (120) may still be missing one or more pins (121).

A missing pin can be as difficult to diagnose and can cause as many problems as a bent pin. But, the absence of a pin will not affect the seating of the tool (100). The absence of a pin presents no obstruction to the seating of the tool (100).

Consequently, it is useful to inspect the tips (121a) of the pins (121) extending through the holes (104a) in the connectors (103) of the tool (100). With the tool (100) in place, it becomes easier to spot an empty hole that has received no pin. If such an empty hole is located, the connector (121) is missing a pin at that location and must be repaired before being placed in service or before receiving a blade.

Figure 5:
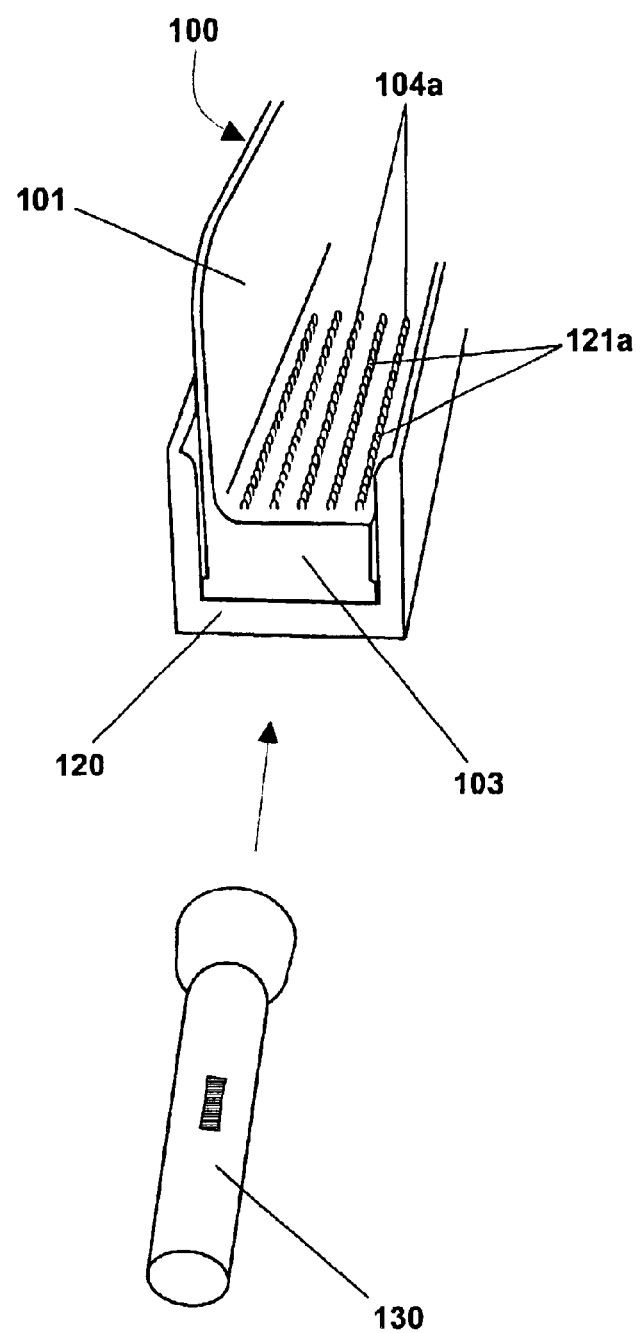
FIG. 5 is an illustration of a technique for evaluating the integrity of pins in a pin connector on a backplane according to another embodiment of the present invention in which the tool of FIG. 1 is installed on a pin connector of a backplane and is used with a light source to help detect missing pins.

FIG. 5 is a further illustration of the technique for evaluating the integrity of pins in a pin connector on a backplane according to another embodiment of the present invention. As shown in FIG. 5, is can be very helpful to shine a light source (130) at an angle on the tips (121a) of the pins which are visible through the open holes (104a) in the connectors (103) of the tool (100). The light source (130) may be, for example, a flashlight. The light is preferably shone on the pin tips (121a) at a low angle, for example, 30 degrees from horizontal.

With the light source (130) illuminating the pin tips (121a), the shiny pin tips (121a) will tend to reflect light from the light source (130). Consequently, a hole (104a) that contains no pin will show up distinctly as a dark hole in a field of shiny, reflective pin tips (121a).

A magnifying glass can also be profitably employed to examine the pin tips (121a) visible through the holes (104a) in the search for missing pins. A magnifying glass can be used with or without the light source (130) illustrated in FIG. 5.

Figure 6:
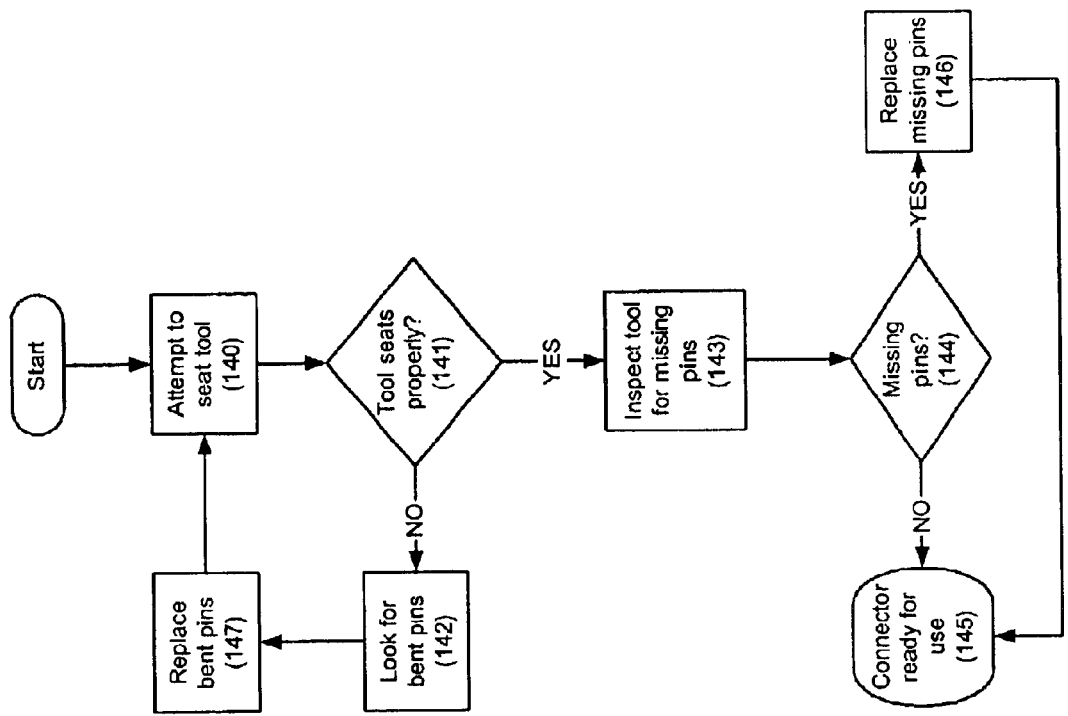
FIG. 6 is a flowchart illustrating a method of testing a pin connector on a backplane according to an embodiment of the present invention.

FIG. 6 is a flowchart illustrating a method of testing a pin connector on a backplane according to an embodiment of the present invention. As shown in FIG. 6, the method begins with an attempt to seat the tool described above. (140). As noted, the tool cannot be forced.

If the tool does not seat properly (141), the tool is removed and the connector is examined for bent pins (142). When the bent pins are located, they can be replaced (147). The method can then return to an attempt to seat the tool (140).

When the tool seats properly (141), the upper surface of the tool is inspected for missing pins. As explained above, one can detect missing pins by looking for an empty hole in the upper surface of the connector (103; FIG. 4) of the tool.

If missing pins are detected (144), those missing pins can be replaced (146). When all missing pins are replaced, or if no missing pins are identified, the connector is ready for use (145).

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A tool for evaluating a pin connector of a backplane, said tool comprising at least one connector having receptacles for receiving pins of a pin connector of a backplane, said receptacles being open at both ends so that ends of said pins are visible in said receptacles when said tool is seated on said pin connector.

2. The tool of claim 1, further comprising a backing plate attached to said at least one connector.

3. The tool of claim 2, wherein said backing plate is integrally formed with said connector.

4. The tool of claim 1, further comprising guides for retaining keys corresponding to keys in said pin connector of a backplane.

5. The tool of claim 1, wherein said at least one connector comprises a plurality of connectors.

6. The tool of claim 1, wherein said at least one connector conforms to the Compact Peripheral Component Interconnect (cPCI) standard.

7. A method of making a tool for evaluating a pin connector of a backplane, said method comprising forming at least one connector having receptacles for receiving pins of a pin connector of a backplane, said receptacles being open at both ends so that ends of said pins are visible in said receptacles when said tool is seated on said pin connector.

8. The method of claim 7, further comprising attaching a backing plate to said at least one connector.

9. The method of claim 7, further comprising integrally forming a backing plate with said connector.

10. The method of claim 7, further comprising forming guides on said tool for retaining keys corresponding to keys in said pin connector of a backplane.

11. The method of claim 7, wherein said at least one connector comprises a plurality of connectors.

12. The method of claim 7, wherein said forming at least one connector further comprises forming at least one connector that conforms to the Compact Peripheral Component Interconnect (cPCI) standard.

13. A method of evaluating a pin connector of a backplane, said method comprising attempting to seat a tool on said pin connector, said tool comprising at least one connector having receptacles for receiving pins of a pin connector of a backplane, said receptacles being open at both ends so that ends of said pins are visible in said receptacles when said tool is seated on said pin connector.

14. The method of claim 13, further comprising inspecting said pin connector for bent pins if said tool does not seat on said pin connector.

15. The method of claim 14, further comprising repairing any bent pins.

16. The method of claim 13, further comprising inspecting said pin connector with said tool seated on said pin connector to determine if any pins are missing from said pin connector.

17. The method of claim 16, wherein said inspecting is performed with a light source shining on said tool.

18. The method of claim 17, wherein light from said light source strikes said tool at approximately a 30-degree angle from horizontal.

19. The method of claim 17, wherein said light source comprises a flashlight.

20. The method of claim 19, wherein said flashlight is held at approximately a 30-degree angle with respect to horizontal.

21. The method of claim 16, wherein said inspecting is performed with a magnifying glass.

22. The method of claim 21, wherein said inspecting is performed with a light source shining on said tool.

23. The method of claim 22, wherein light from said light source strikes said tool at approximately a 30-degree angle from horizontal.

24. The method of claim 16, further comprising replacing any missing pins.

25. A tool for evaluating a pin connector of a backplane, said tool comprising at means for receiving pins of a pin connector of a backplane such that said means will be obstructed from receiving said pins of said pin connector if any of said pins is bent.

26. The tool of claim 25, wherein said means, when receiving said pins of said pin connector, leaves ends of said pins visible.

27. The tool of claim, 25, further comprising handle means, connected to said means for receiving said pins, for handling said means for receiving said pins.

28. The tool of claim 27, wherein said handle means are integrally formed with said means for receiving said pins.

29. The tool of claim 25, further comprising means for retaining keys corresponding to keys in said pin connector of a backplane.

* * * * *